(12) United States Patent
Honeck et al.

(10) Patent No.: US 8,731,669 B2
(45) Date of Patent: May 20, 2014

(54) BIPOLAR LEAD CONTAINING HV AND LV SIGNAL CAPABILITY

(75) Inventors: Jordon D. Honeck, Maple Grove, MN (US); Andrew J. Ries, Lino Lakes, MN (US); Karel F. A. A. Smits, Munstergeleen (NL)

(73) Assignee: Medtronic, Inc., Minneapolis, MN (US)

( * ) Notice: Subject to any disclaimer, the term of this patent is extended or adjusted under 35 U.S.C. 154(b) by 1860 days.

(21) Appl. No.: 11/764,886

(22) Filed: Jun. 19, 2007

(65) Prior Publication Data

US 2008/0319503 A1 Dec. 25, 2008

(51) Int. Cl.
*A61N 1/05* (2006.01)
*A61N 1/375* (2006.01)

(52) U.S. Cl.
CPC .................................... *A61N 1/3752* (2013.01)
USPC ............................................................ 607/37

(58) Field of Classification Search
CPC .................................................... A61N 1/0504
USPC ............... 607/36–38, 4–5, 122–123; 439/909
See application file for complete search history.

(56) References Cited

U.S. PATENT DOCUMENTS

| | | | |
|---|---|---|---|
| 4,180,078 A | 12/1979 | Anderson | |
| 5,188,105 A | 2/1993 | Keimel | |
| 5,470,345 A | 11/1995 | Hassler et al. | |
| 6,038,472 A * | 3/2000 | Williams et al. | 607/5 |
| 6,044,302 A | 3/2000 | Persuitti et al. | |
| 6,434,430 B2 | 8/2002 | Borgersen et al. | |
| 6,675,049 B2 * | 1/2004 | Thompson et al. | 607/60 |
| 2004/0064164 A1 * | 4/2004 | Ries et al. | 607/37 |
| 2004/0078062 A1 | 4/2004 | Spadgenske | |
| 2006/0020316 A1 * | 1/2006 | Martinez et al. | 607/122 |

* cited by examiner

*Primary Examiner* — Carl H Layno
*Assistant Examiner* — Erica Lee
(74) *Attorney, Agent, or Firm* — Reed A. Duthler (57) ABSTRACT

An implantable medical device system includes a medical electrical lead having a connector assembly and a connector bore for receiving the lead connector assembly. The lead includes a distal portion having a first outer diameter and a distal sealing member, an intermediate portion having a second outer diameter smaller than the first outer diameter, and a connector pin extending from the intermediate portion, the connector pin having an outer diameter corresponding to a DF-1 standard.

10 Claims, 7 Drawing Sheets

BIPOLAR LEAD CONTAINING HV AND LV SIGNAL CAPABILITY

FIELD OF THE INVENTION

The present invention generally relates to an implantable, medical, electrical lead and associated implantable cardioverter-defibrillator (ICD) and more particularly to a lead connector assembly and corresponding device connector module.

BACKGROUND

ICDs deliver relatively high-energy cardioversion and/or defibrillation shocks to a patient's heart when a malignant tachyarrhythmia, e.g., atrial or ventricular fibrillation, is detected. ICDs typically operate in conjunction with one or more leads carrying a coil electrode(s) for delivering high-voltage shocking pulses. In addition to a coil electrode, the lead may carry pace/sense electrodes for sensing intracardiac electrogram signals (EGM) or subcutaneous ECG signals and for delivering low-voltage pacing pulses.

Numerous ICD systems are commercially available and may be used in conjunction with a variety of lead systems. Industry standards have been developed to prevent the insertion and electrical coupling of a high voltage lead terminal to a low voltage ICD connector module terminal and vice versa. Improper connection of electrical leads to the ICD may cause device damage, inappropriate or failed operation of the ICD, and undue risk to the patient.

BRIEF DESCRIPTION OF THE DRAWINGS

Aspects and features of the present invention will be appreciated as the same becomes better understood by reference to the following detailed description of the embodiments of the invention when considered in connection with the accompanying drawings, wherein.

DETAILED DESCRIPTION

In the following description, references are made to illustrative embodiments for carrying out the invention. It is understood that other embodiments may be utilized without departing from the scope of the invention. For purposes of clarity, the same reference numbers are used in the drawings to identify similar elements. Unless otherwise indicated, drawing elements are not drawn to scale.

Figure 1A:
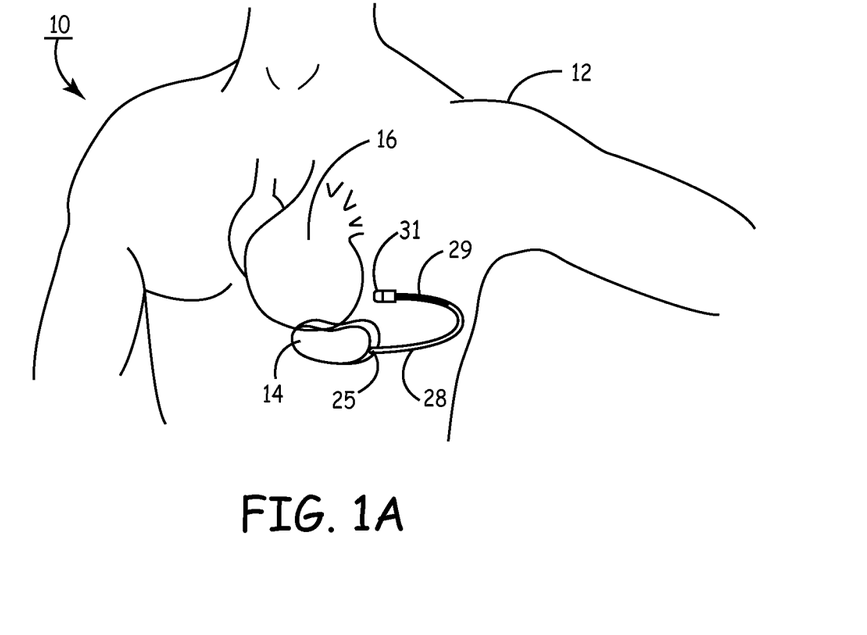
FIG. 1A is a schematic diagram of a subcutaneous medical device implanted in a patient according to one embodiment of the present invention.

FIG. 1A is a schematic diagram of a subcutaneous implantable cardioverter defibrillator (SubQ ICD) 10 implanted in a patient 12 according to one embodiment of the present invention. SubQ ICD 10 includes a hermetically sealed housing 14 that is subcutaneously implanted outside a patient's ribcage anterior to the cardiac notch. Implant locations shown in FIG. 1A and other diagrams provided herein are approximate and may not correspond to exact anatomical locations in any given patient. A subcutaneous lead 28 is electrically coupled to circuitry enclosed within housing 14 via a connector module 25 coupled to housing 14. Lead 28 includes a coil electrode 29 for delivering high-voltage cardiversion/defibrillation therapies to heart 16 and a low-voltage pace/sense electrode 31 located at a distal end of lead 28. The distal electrodes 31 and 29 are tunneled subcutaneously from the implant pocket of housing 14 laterally and posteriorly to the patient's back to a location opposite the heart 16 such that the heart is disposed between the housing 14 and the distal coil electrode 29 of subcutaneous lead 28.

To facilitate electrical connection of high-voltage coil electrode 29 and low-voltage pace/sense electrode 31 to device circuitry, lead 28 is provided with a lead connector assembly (not shown In FIG. 1A) that is inserted into a connector bore included in connector module 25. In past practice, a bifurcated lead connector assembly has been used to separately connect the high-voltage coil electrode 29 to a high-voltage connector bore and the low-voltage pace/sense electrode 31 to a low-voltage connector bore, both the high- and low-voltage connector bores formed in connector module 25.

As will be described herein, in one embodiment of the present invention, lead 28 is provided with a single, in-line bipolar connector assembly having a high-voltage connector coupled to high-voltage coil electrode 29 and a low-voltage connector coupled to low-voltage pace/sense electrode 31. SubQ ICD 10 is provided with a connector module having a bipolar in-line connector bore including a high-voltage contact adapted to be electrically coupled to the lead assembly high-voltage connector and a low-voltage contact adapted to be electrically coupled to the lead assembly low-voltage connector.

Figure 1B:
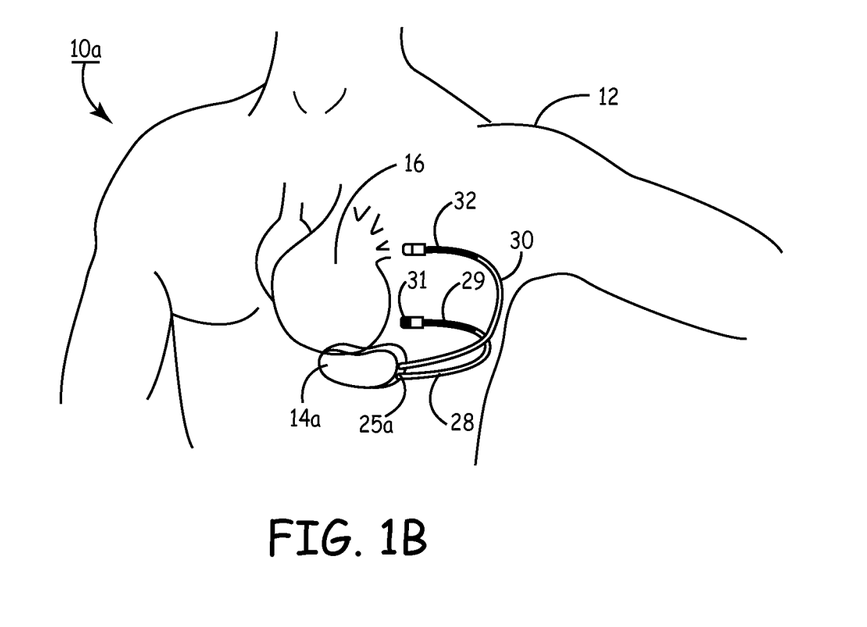
FIG. 1B is a schematic diagram of a SubQ ICD implanted in a patient according to another embodiment of the present invention.

FIG. 1B is a schematic diagram of a SubQ ICD 10a implanted in a patient according to an alternative embodiment of the present invention. SubQ ICD 10a is subcutaneously implanted outside a patient's ribcage anterior to the cardiac notch, as described above in relation to FIG. 1A. Subcutaneous lead 28 is coupled to connector module 25a and extends to a posterior location for positioning coil electrode 29 and pace/sense electrode 31 as described above.

A second subcutaneous lead 30 is coupled to SubQ ICD 10a via connector module 25a and its distal end is tunneled subcutaneously from the implant pocket of housing 14a laterally and posteriorly to the patient's back to a location caudal to subcutaneous lead 28. The use of the second lead 30 having cardioversion/defibrillation coil electrode 32 allows more of the heart mass to be positioned between the housing 14a and the coil electrodes 29 and 32, potentially reducing the defibrillation threshold required to defibrillate the heart 16.

As will be further described herein, connector module 25a is provided with one in-line bipolar connector bore for receiving a connector assembly of lead 28 as described above and a second connector bore including a high-voltage contact for receiving and electrically coupling to a lead connector assembly of subcutaneous lead 30.

Figure 2A:
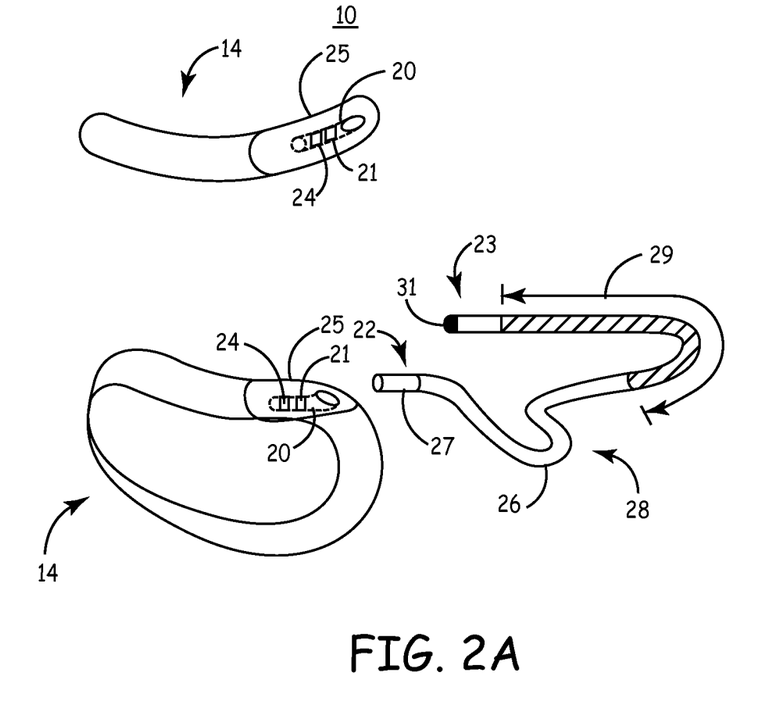
FIG. 2A is a top and plan view of the SubQ ICD 10 and associated lead 28 shown in FIG. 1A.

FIG. 2A is a top and plan view of the SubQ ICD 10 and associated lead 28 shown in FIG. 1A. Connector module 25 is coupled to housing 14 and configured for receiving proximal lead connector assembly 27 of subcutaneous lead 28, thereby electrically connecting the lead 28 to circuitry enclosed within housing 14. It is desirable to minimize the overall size of the SubQ ICD 10 to promote ease of subcutaneous implantation and patient comfort. As such, it is desirable to minimize the overall size and bulk of the lead connector assembly 27 and connector module 25. Furthermore, it is desirable to promote proper device function and patient safety by safeguarding against insertion of improper lead connector assemblies within the SubQ ICD connector module 25.

Housing 14 may be constructed of stainless steel, titanium or ceramic as described in U.S. Pat. No. 4,180,078 "Lead Connector for a Body Implantable Stimulator" to Anderson and U.S. Pat. No. 5,470,345 "Implantable Medical Device with Multi-layered Ceramic Enclosure" to Hassler, et al. The electronic circuitry in housing 14 includes circuitry for performing any desired sensing and/or therapy delivery function (s), such as detection of a tachyarrhythmia from sensed ECG signals and delivering cardioversion/defibrillation therapy, as well as post-shock pacing as needed while the heart recovers. The circuitry and functionality of SubQ ICD 10 may correspond to tachycardia detection and therapy delivery devices generally disclosed, for example, in U.S. Pat. No. 5,188,105 (Keimel), hereby incorporated herein by reference in its entirety.

Lead 28 includes a lead body 26 that extends from lead connector assembly 27 at the proximal end 22 of lead 28 to a distal end 23 of the lead 28. Distal pace/sense electrode 31 is positioned at the distal end 23 of lead 28. A coil electrode 29 is positioned near the distal end 23 of the lead, just proximal to the pace/sense electrode 31 and extends proximally along the lead body 26. The coil electrode 29 and pace/sense electrode 31 are typically formed of platinum, titanium or platinum iridium alloy. The proximal connector assembly 27 includes electrical connectors that are electrically coupled to insulated conductor(s) (not shown) extending the length of the lead body 26 and electrically coupled to the respective coil electrode 29 and pace/sense electrode 31.

Connector module 25 is provided with a single, in-line connector bore 20 for receiving lead connector assembly 27. Connector bore 20 includes two electrical contacts 21 and 24 for electrically coupling to connectors included in connector assembly 27. Electrical contact 21 is a low-voltage contact that becomes electrically coupled to low-voltage pace/sense electrode 31 when connector assembly 27 is inserted into bore 20. Electrical contact 24 is a high-voltage contact that becomes electrically coupled to high-voltage electrode 29 when connector assembly 27 is inserted into bore 20. The high-voltage contact 24 is electrically coupled to high-voltage output circuitry enclosed within housing 14, and the low-voltage contact 21 is electrically coupled to sensing circuitry and low-voltage output circuitry enclosed in housing 14. The bipolar connector assembly 27 and in-line connector module 25 will be described in detail herein in conjunction with FIG. 3 and FIG. 7 respectively. While a single high-voltage electrode 29 and a single low-voltage electrode 31 are shown on lead 28, it is recognized that lead 28 may be provided with one or more high-voltage electrodes coupled to a high-voltage connector included in connector assembly 27 and one or more low-voltage electrodes coupled to a low-voltage connector included in connector assembly 27.

Figure 2B:
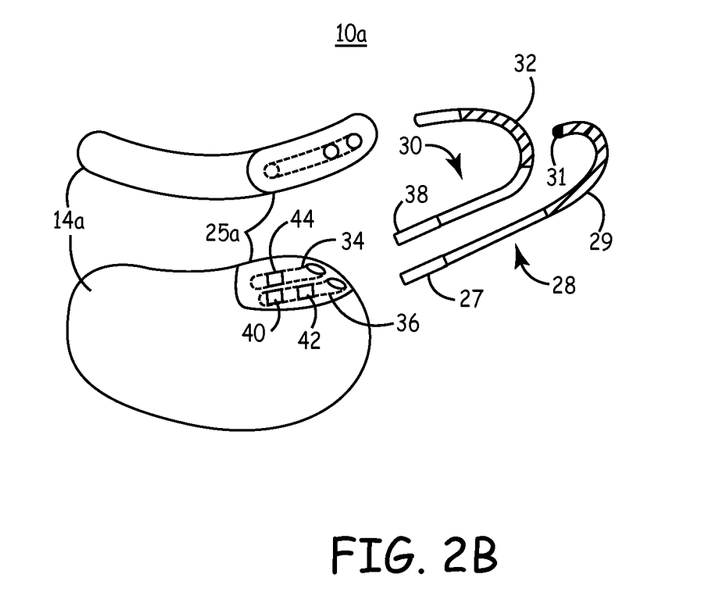
FIG. 2B is a top and plan view of the SubQ ICD 10a shown in FIG. 1B.

FIG. 2B is a top and plan view of the SubQ ICD 10a shown in FIG. 1B. Connector module 25a is coupled to housing 14a and configured with two connector bores 34 and 36. The first connector bore 36 is configured as a bipolar in-line connector bore for receiving proximal lead connector assembly 27 of subcutaneous lead 28 and electrically connecting both the high-voltage coil electrode 29 and the low-voltage pace/sense electrode 31 to circuitry enclosed within housing 14a, as generally described above in conjunction with connector bore 20 of FIG. 2A.

The second connector bore 34 is configured to receive lead connector assembly 38 of subcutaneous lead 30. Connector bore 34 includes a high-voltage contact 44 for electrically coupling high-voltage electrode 32 to high-voltage output circuitry enclosed within housing 14a. Connector bore 34 may be configured as a standard unipolar high-voltage connector bore conforming to the Standard ISO 11318:1993(E) of the International Organization for Standards, hereafter referred to as the "DF-1 standard" or merely "DF-1". Alternatively, connector bore 34 may be provided as a custom unipolar connector bore as will be described in detail herein in conjunction with FIG. 4. In either case, lead connector assembly 38 may be configured as a DF-1 standard connector assembly. Alternatively, connector assembly 38 may be provided as a custom connector assembly, as described below in conjunction with FIG. 3, which is compliant with a unipolar DF-1 connector bore.

Figure 3:
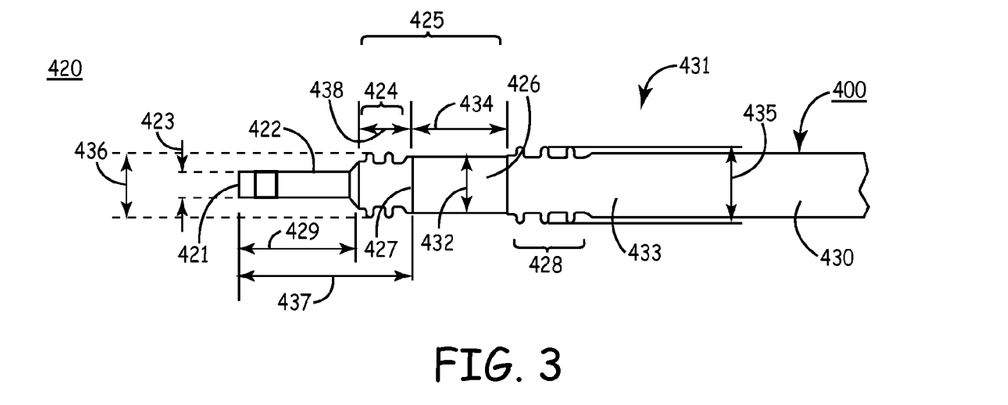
FIG. 3 is a side view of a lead connector assembly.

FIG. 3 is a side view of a lead 400 having an in-line lead connector assembly 420 according to one embodiment of the invention. Lead 400 includes a lead body 430 extending between a proximal end 431 to a distal lead end (not shown). The connector assembly 420 extends from the lead body proximal end 431 and includes a high voltage connector pin 422 which is electrically coupled to one or more conductors extending within lead body 430 to one or more coil electrodes carried by lead body 430 for delivering high voltage cardioversion/defibrillation pulses. Lead 400 may correspond, for example, to lead 28 shown in FIG. 1A. The connector pin 422 is sized to conform, at least in part, to the DF-1 standard. As such, connector pin 422 is provided with an outer diameter 423 of 0.049", within the DF-1 required tolerance. The connector pin 422 is provided with a length 429 that may or may not correspond to the DF-1 standard. In one embodiment, pin 422 is provided with a length less than the DF-1 standard, for example a length 429 is 0.205" as compared to a DF-1 standard length of 0.225 inches. Connector pin 422 may be provided with an open lumen (not shown in FIG. 3) that extends to an inner lumen of lead body 430 for the introduction of a stylet.

While the DF-1 standard is applied to the outer dimension 423 of the connector pin 422, other components included in connector assembly 420 do not conform to the DF-1 standard as will be described herein. For example, connector assembly 420 includes a first set of sealing rings 424 proximate and distal to the connector pin 422. The first sealing rings 424 are sized to conform to the Standard ISO 5841-3:1992(E) of the International Organization for Standards, hereinafter referred to as the "IS-1 standard" or merely "IS-1". As such, the first set of sealing rings 424 are formed having an outer diameter 436 of 0.125" and occupy an axial length 438 of 0.100" along the connector assembly. Sealing rings 424 are formed of a biocompatible resilient polymer such as, but not limited to, silicone.

The connector assembly 420 additionally includes a low voltage connector ring 426 distally adjacent to the first set of sealing rings 424. The connector ring 426 and the sealing rings 424 form an intermediate connector assembly portion 425 which is sized along its outer dimensions to conform to the IS-1 standard. As such, connector ring 426 is provided with an outer diameter 432 of 0.105 inches. In one embodiment, connector ring 426 is provided with a length 434 of 0.160 inches. The length 434 of connector ring 426 may or may not conform to the IS-1 standard.

Likewise the spacing 437 between the proximal tip 421 of the connector pin 422 and the proximal leading edge 427 of the connector ring 426 may or may not conform to the spacing of 0.400 inches between a connector pin tip and connector ring leading edge as defined by the IS-1 standard. This spacing may be less than or greater than the IS-1 standard in various embodiments of the invention. In one embodiment, the connector ring leading edge 427 is spaced less than the IS-1 standard at 0.319 inches from the proximal connector pin tip 421.

The connector assembly 420 includes a second set of distal sealing rings 428 located proximate to and distal from the connector ring 426. The distal sealing rings 428 are formed along a connector assembly distal portion 433 adjacent the proximal end 431 of lead body 430. Distal sealing rings 428 and distal portion 433 are sized to conform to the DF-1 standard. As such, sealing rings 428 are provided with an outer diameter 435 of 0.150 inches. The lead body 430 may be formed of any flexible insulating material such as silicone rubber or polyurethane and may be formed as generally described in U.S. Pat. No. 6,434,430 "Co-Extruded, Multi-Lumen Medical Lead" (Borgersen, et al.), hereby incorporated herein by reference in its entirety. Lead connector assembly 420, however, may be implemented in combination with a variety of lead body designs including multi-lumen lead body designs, single lumen lead body designs, and "over-the-wire" designs.

Figure 4:
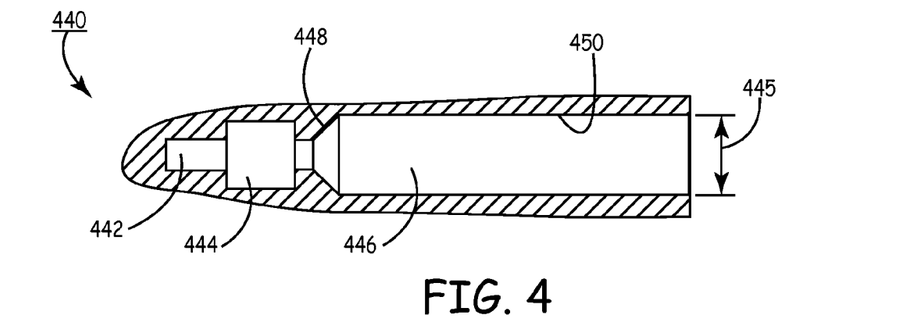
FIG. 4 is a side cut-away view of a unipolar connector module of a medical device.

FIG. 4 is a side cut-away view of a connector module 440 including a unipolar connector bore 446 according to one embodiment of the present invention. Connector bore 446 is compatible with the lead connector assembly 420 described above in conjunction with FIG. 3. A high-voltage contact 444, which may be embodied as a set screw block, is used to secure the lead in the bore 446 and provide electrical connection to the high voltage connector pin 422 of lead 420 (FIG. 3). Pin receptacle 442 and set-screw block 444 are adapted to receive the connector pin 422 and are therefore sized with an inner diameter conforming to the DF-1 standard. The connector bore 446 is formed by inner surface 450 having an inner diameter 445 sized to interface with the DF-1 compliant second, distal sealing rings 428 of lead connector assembly 420. As such, connector bore 446 is provided with an inner diameter 445 of 0.137 inches in one embodiment, which is compliant with the DF-1 standard. Connector bore 446 narrows at neck portion 448 to form the DF-1 compatible pin receptacle 442.

Figure 5:
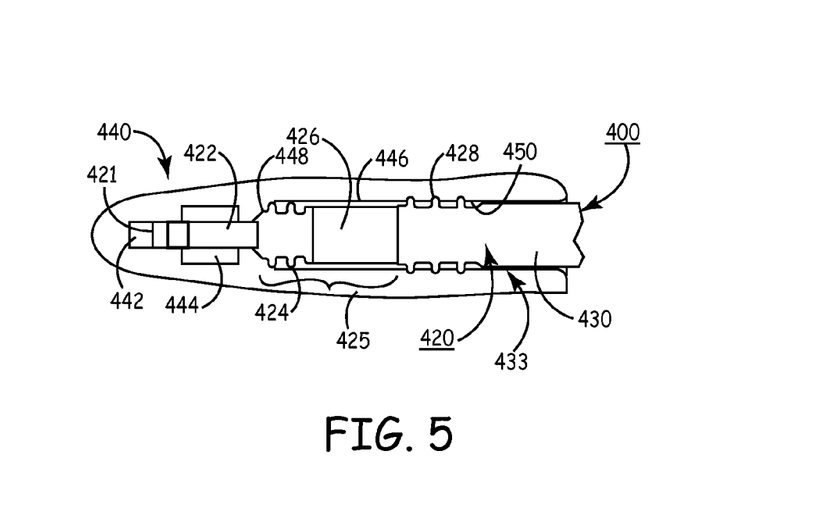
FIG. 5 is a side cut-away view of the connector assembly of FIG. 3 inserted in the unipolar connector module of FIG. 4.

FIG. 5 is a side cut-away view of the lead connector assembly 420 of FIG. 3 inserted in the connector module 440 of FIG. 4. As described above, the connector bore 446 is sized with an inner diameter 445 (shown in FIG. 4) for receiving the distal portion 433 of connector assembly 420 and forming a fluid-resistant interference fit between bore inner surface 450 and the second, distal sealing rings 428. The lead connector assembly intermediate portion 425 including first, proximal sealing rings 424 and connector ring 426, sized to conform to the IS-1 standard, is smaller in diameter than the bore 446 and therefore do not interface with the inner surface 450 of bore 446. High voltage pin connector 422 is advanced into pin receptacle 442 and secured and electrically coupled to high voltage contact 422.

Figure 6:
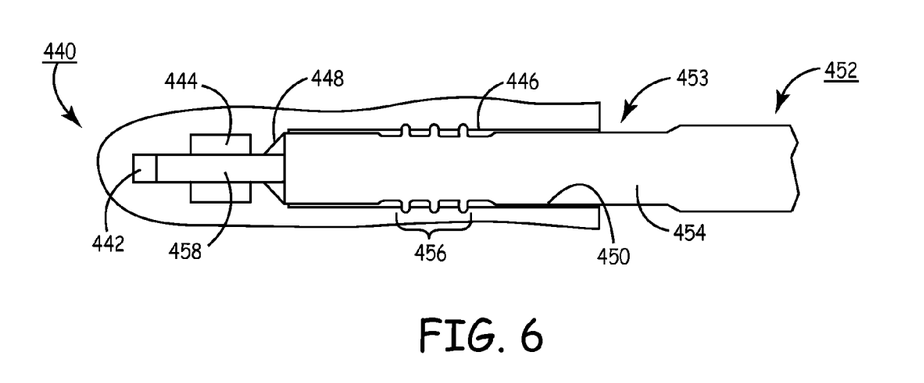
FIG. 6 is a side cut-away view of a standard DF-1 unipolar lead connector assembly inserted into the unipolar connector module of FIG. 4.

FIG. 6 is a side cut-away view of a unipolar DF-1 lead connector assembly inserted into the unipolar connector module 440 of FIG. 4. Lead 452 includes a proximal connector assembly 453 which fully complies with the DF-1 standard. Connector assembly 453, extending from the proximal end of lead body 454, includes a set of sealing rings 456 and a connector pin 458. The diameter of pin receptacle 442 of custom connector module 440 conforms to the DF-1 standard and can therefore properly receive connector pin 458. The high voltage contact 444 provides electrical connection to connector pin 458 and secures connector assembly 453 within connector module 440. The sealing rings 456 interface with the inner surface 450 of bore 446, thereby forming a fluid-resistant seal. As such, while the unipolar connector module 440 does not fully conform to the DF-1 standard, module 440 is compatible with a DF-1 lead connector.

With respect to the embodiment shown in FIG. 2B, the lead connector assembly 38 of high-voltage subcutaneous lead 30 may be embodied as a DF-1 lead connector assembly 453 shown in FIG. 6. Connector bore 36 of the connector module 25a shown in FIG. 6 may be embodied as the custom unipolar connector bore 440, as shown in FIG. 6. Alternatively, the lead connector assembly 38 may be embodied as the custom bipolar in-line connector assembly 420 shown in FIG. 3 with the connector ring 426 unused. While connector module 440 is shown having a single connector bore 446, it is recognized that bore 446 may be provided with other unipolar, bipolar, and/or multi-polar connector bores in a single module 440.

Figure 7:
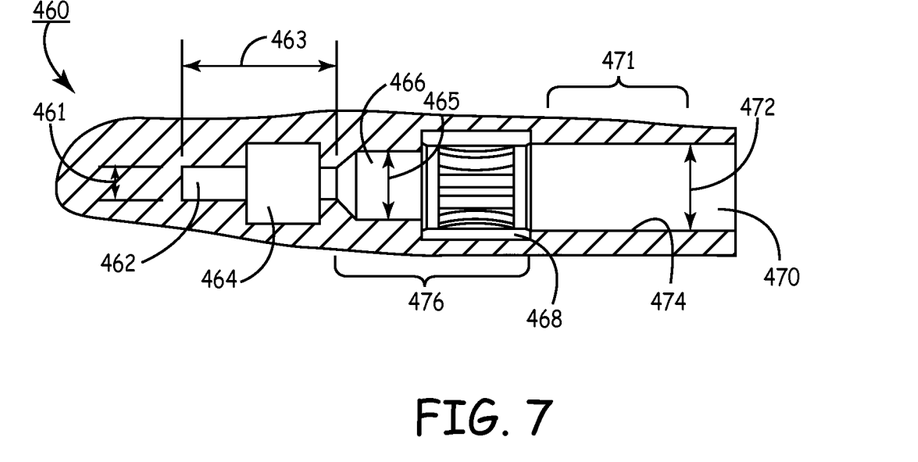
FIG. 7 is a side cut-away view of a bipolar connector module of a medical device.

FIG. 7 is a side cut-away view of a connector module 460 of a medical device according to another embodiment of the present invention. The connector module 460 includes a bipolar in-line electrical connector bore 470 compatible with the custom lead connector assembly 420 described above in conjunction with FIG. 3. Connector module 460 is adapted to receive the connector assembly 420 (FIG. 3) and form electrical connections with both the high voltage electrical lead connector pin used to couple to cardioversion/defibrillation electrodes and a second low voltage pacing/sensing lead connector ring used to couple to pacing/sensing electrodes carried by lead 400. Connector module 460 includes a pin receptacle 462 sized to receive connector pin 422 (FIG. 4). Pin receptacle 462 includes a high-voltage contact 464, which may be embodied as a set screw block, for securing the lead connector assembly 420 in the connector module 460 and provide electrical connection to the connector pin 422. Pin receptacle 462 is provided with an inner diameter 461 that corresponds to the DF-1 standard. The overall length 463 of the pin receptacle 462 may or may not correspond to the length of a pin receptacle and high-voltage contact included in a DF-1 standard connector bore. For example, the overall length 463 of the pin receptacle 462 may be less than or greater than the pin receptacle length in a DF-1 standard connector module. In one embodiment, length 463 is 0.235 inches. The dimensions of pin receptacle 462 may correspond to the dimension of pin receptacle 442 shown in FIG. 4.

Connector module 460 further includes an intermediate portion 476 including an intermediate bore portion 466 and a low voltage contact 468. Low voltage contact 468 is adapted to form an electrical connection with connector ring 426 of lead 420. Contact 468 may be embodied as a multi-beam contact, a set screw block, or the like. The inner diameter of the intermediate bore portion 466 is sized to correspond to an IS-1 connector module. In particular, bore portion 466 is provided having an inner diameter 465 of approximately 0.106 inches. Connector module 460 includes a distal bore portion 471 formed by inner surface 474 having a larger inner diameter 472 than the intermediate bore portion 466. In particular, distal bore portion 471 is provided with an inner diameter 472 that corresponds to a DF-1 connector module. Specifically, inner diameter 472 is approximately 0.137 inches.

Figure 8:
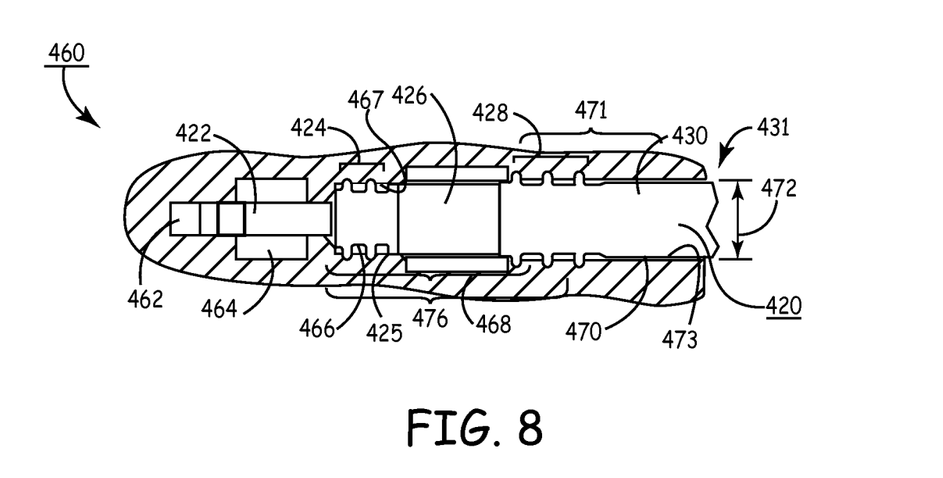
FIG. 8 is a side cut-away view of the connector assembly of FIG. 3 inserted in the connector module of FIG. 7.

FIG. 8 is a side cut-away view of the in-line bipolar connector assembly 420 of FIG. 3 inserted in the connector module 460 of FIG. 7. The connector bore 470 is sized along distal bore portion 471 with an inner diameter 472 for receiving distal portion 433 of lead connector assembly 420 and forming a fluid-resistant interference fit between inner surface 473 and second, distal sealing rings 428. The intermediate lead connector assembly portion 425 interfaces with the intermediate portion 476 of connector bore 470. Specifically, the first, proximal sealing rings 424 interface with the inner surface 467 of intermediate bore portion 466 to form a fluid resistant seal. Connector ring 426 forms an electrical and mechanical connection with low voltage contact 468, shown as a multi-beam contact. Connector pin 422 is inserted into pin receptacle 462 and forms an electrical connection with high voltage contact 464. As such, connector module 460 allows electrical connection to an in-line connector assembly including both a high-voltage connector (pin 422) and a low-voltage connector (ring 426).

With reference to the embodiment shown in FIG. 2A, connector module 25 having in-line connector bore 20 may correspond to the connector module 460, and lead connector assembly 27 may correspond to the bipolar, in-line connector assembly 420 of FIG. 3. It is recognized that connector module 460 may include additional connector bores. For example, connector module 25a shown in FIG. 2B includes a bipolar, in-line connector bore 34 that may be configured as the custom bipolar connector bore 470 shown in FIG. 7 and a second connector bore 36 configured as the custom unipolar connector bore 446 shown in FIG. 4.

Figure 9:
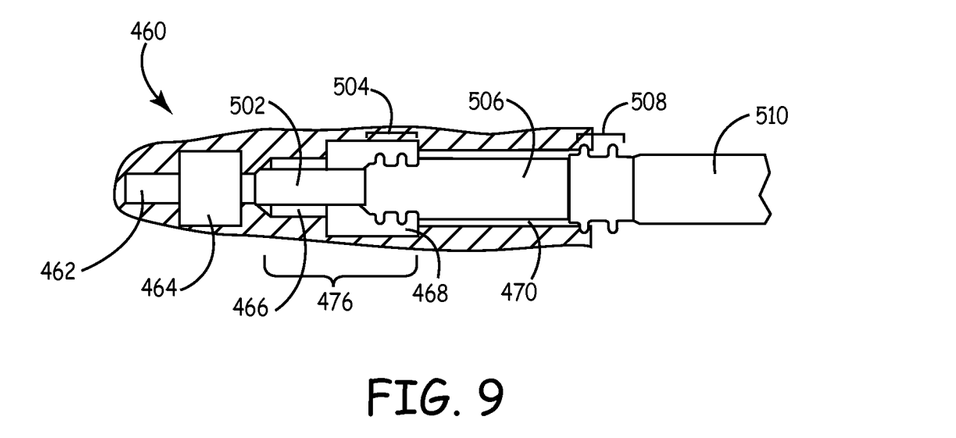
FIG. 9 is a side cut-away view of an IS-1 lead connector assembly being inserted into the connector module of FIG. 7.

FIG. 9 is a side cut-away view of an IS-1 lead connector assembly being inserted into the connector module 460 of FIG. 7. Lead 510 includes a connector pin 502, first proximal sealing rings 504, a connector ring 506 and second distal sealing rings 508 all sized and positioned axially along lead 510 in full compliance with the IS-1 standard. Even though the first sealing rings 504 and the connector ring 506 would fit within the intermediate portion 476 of connector bore 470, the lead 510 is prevented from being fully inserted into connector bore 470 due to the size mismatch of the IS-1 pin connector 502 and the pin receptacle 462, which is smaller in diameter than the IS-1 pin connector diameter. Thus, a low voltage IS-1 lead cannot be inadvertently connected to the high-voltage contact 464 of the in-line bipolar connector module 460.

Figure 10:
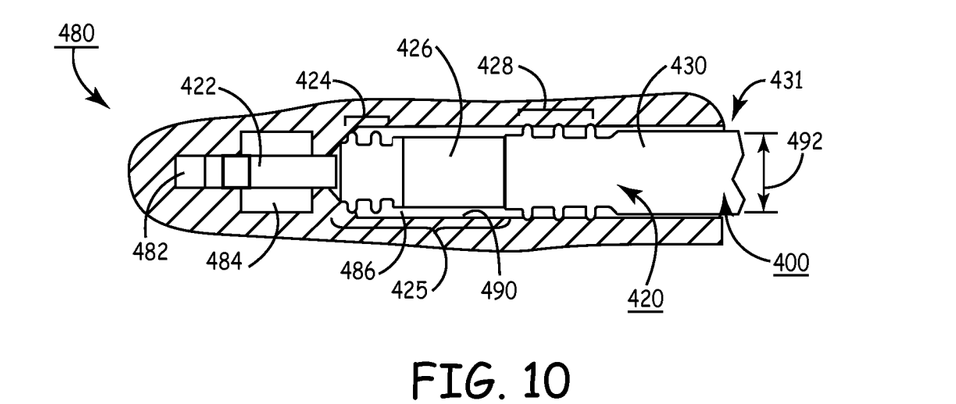
FIG. 10 is a side cut-away view of the lead connector assembly shown in FIG. 3 inserted into a standard DF-1 unipolar connector module.

FIG. 10 is a side cut-away view of the bipolar in-line lead connector assembly 420 shown in FIG. 3 inserted into a DF-1 standard unipolar connector module 480. Connector module 480 includes a pin receptacle 482 having a high-voltage contact 484 embodied as a set-screw block and a connector bore 486 formed by an inner surface 490 having an inner diameter 492. The pin receptacle 482 and bore 486 are sized to be fully compliant with the DF-1 standard. As such, connector pin 422 of connector assembly 420, sized with an outer diameter compliant with the DF-1 standard, can be fully inserted into pin receptacle 482 for electrical and mechanical coupling with the high voltage contact 484. Intermediate portion 425 having narrower outer dimensions than the DF-1 sized bore 486 does not interface with inner surface 490 of bore 486. More specifically, first sealing rings 424 and low voltage connector ring 426 "float" within bore 486. However, second, distal sealing rings 428, having an outer diameter corresponding to the DF-1 standard, interface with inner surface 490 thereby forming a fluid resistant seal. Thus, the bipolar, in-line connector assembly 420 is compliant with a standard DF-1 module 480.

Figure 11:
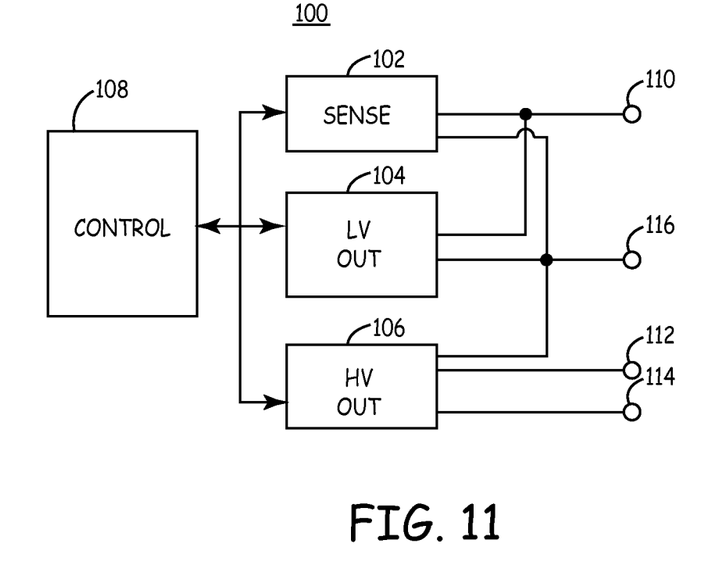
FIG. 11 is a functional block diagram of circuitry enclosed in the housing of an implantable medical device according to an embodiment of the present invention.

FIG. 11 is a functional block diagram of circuitry enclosed in the housing of an implantable medical device, such as any of the SubQ ICDs shown in FIGS. 1A-2B. Circuitry 100 includes sensing circuitry 102, low voltage output circuitry 104, high voltage output circuitry 106, and a control module 108. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

Sensing circuitry 102 is coupled to low-voltage terminal 110 and a common terminal 116 (which may be coupled to the device housing) to receive ECG/EGM signals from one or more sensing electrodes coupled to the low-voltage terminal 110. Low voltage terminal 110 is coupled to a low-voltage contact in a connector module, such as contact 468 shown in FIG. 7, for electrically coupling sensing circuitry 102 to one or more low-voltage sensing electrodes carried by a lead extending from the connector module.

In response to sensed heart rhythms, the control module 108 may enable therapy delivery by either low-voltage output circuitry 104 or high-voltage output circuitry 106. Low-voltage output circuitry 104 is coupled to common terminal 116 and to the low-voltage terminal 110. Low-voltage terminal 110 is electrically coupled to a low-voltage contact, such as contact 468 in FIG. 7 as described above, and thereby to one or more low-voltage electrodes for delivering pacing pulses to a patient's heart. High-voltage output circuitry 106 is coupled to one or more high voltage terminals 112 and 114. High voltage terminals 112 and 114 are coupled to high-voltage contacts included in a connector module, such as high voltage contact 444 shown in FIG. 4 or high voltage contact 464 shown in FIG. 7.

It is recognized that the specific architecture and circuitry for implementing the device functionality may vary widely between implantable devices. It is further recognized that although embodiments described herein refer primarily to a subcutaneous device and associated subcutaneous leads, the lead connector assembly and connector module embodiments described herein may be implemented in any implantable medical device including low-voltage and high-voltage channels, including devices functioning with transvenous or epicardial leads.

Thus, lead connector assemblies and device connector modules have been presented in the foregoing description with reference to specific embodiments. It is appreciated that various modifications to the referenced embodiments may be made without departing from the scope of the invention as set forth in the following claims.

The invention claimed is:

1. An implantable medical device system, comprising:
 a medical electrical lead having a lead body extending from a proximal end to a distal end, the proximal end having an in-line connector assembly, the in-line connector assembly comprising;
 a connector pin having an outer diameter corresponding to a DF-1 standard, a first sealing member proximate and distal to the connector pin and having an outer diameter corresponding to an IS-1 standard, a connector ring proximate and distal to the first sealing member and having an outer diameter corresponding to the IS-1 standard, and a second sealing member proximate and distal to the connector ring and having an outer diameter corresponding to the DF-1 standard;

a device comprising a housing and a connector module coupled to the housing, the connector module comprising an in-line connector bore configured for receiving the in-line connector assembly, the in-line connector bore comprising:

a lead pin receptacle sized to receive the connector pin, and a first bore portion sized to form a fluid-resistant interface with the second sealing ring.

2. The system of claim 1 wherein the in-line connector bore further comprises an intermediate portion located between the pin receptacle and the first bore portion and configured for receiving the first sealing member and the connector ring, the intermediate portion comprising:

a second bore portion sized to form a fluid resistant interface with the first sealing member, and a contact sized to form an electrical connection with the connector ring.

3. The implantable medical device system of claim 2 wherein the contact is coupled to a low-voltage terminal of the device.

4. The implantable medical device system of claim 1 wherein the medical electrical lead includes a high-voltage electrode and a low-voltage electrode and the connector pin is electrically coupled to the high-voltage electrode and the connector ring is electrically coupled to the low-voltage electrode.

5. The implantable medical device system of claim 1 wherein the lead pin receptacle includes an electrical contact for electrically coupling to the connector pin, the electrical contact coupled to a high-voltage terminal of the device.

6. An implantable medical device system, comprising:

a medical electrical lead comprising a lead body extending from a proximal end to a distal end and a connector assembly extending from the lead body proximal end, the connector assembly comprising:

a distal portion having a first outer diameter and a distal sealing member; an intermediate portion having a second outer diameter smaller than the first outer diameter, and a connector pin extending from the intermediate portion, the connector pin having an outer diameter corresponding to a DF-1 standard; and a device comprising a housing and a connector module coupled to the housing, the connector module comprising a connector bore for receiving the connector assembly, the connector bore comprising:

a pin receptacle sized to receive the connector pin, and a first bore portion distal to the pin receptacle sized to receive the distal portion and form a fluid-resistant interface with the distal sealing member;

wherein the connector bore further comprises an intermediate portion between the in receptacle and the first bore portion, the connector bore intermediate portion sized to interface with the connector assembly intermediate portion;

wherein the connector assembly intermediate portion comprises a connector ring and the connector bore intermediate portion comprises an electrical contact sized to electrically couple to the connector ring;

wherein the connector assembly intermediate portion further comprises a proximal sealing member positioned between the connector pin and the connector ring, the proximal sealing member sized to form a fluid-resistant interface with the connector bore intermediate portion; and wherein the connector assembly intermediate portion having an outer diameter conforming to an IS-1 standard and the connector bore intermediate portion having an inner diameter conforming to the IS-1 standard.

7. The system of claim 6 wherein the medical electrical lead further comprises a high-voltage electrode and a low-voltage electrode and the connector pin is electrically coupled to the high-voltage electrode and the connector ring is electrically coupled to the low-voltage electrode.

8. The system of claim 7 wherein the pin receptacle includes a contact coupled to a high voltage terminal of the device.

9. The system of claim 8 wherein the electrical contact of the connector bore intermediate portion is coupled to a low voltage terminal of the device.

10. An implantable medical device lead, comprising:

a lead body extending from a proximal end to a distal end, and an in-line connector assembly extending from the lead body proximal end comprising:

a connector pin having an outer diameter corresponding to a DF-1 standard, a first sealing member proximate and distal to the connector pin and having an outer diameter corresponding to an IS-1 standard, a connector ring proximate and distal to the first sealing member and having an outer diameter corresponding to the IS-1 standard, and a second sealing ring proximate and distal to the connector ring and having an outer diameter corresponding to the DF-1 standard.

* * * * *

UNITED STATES PATENT AND TRADEMARK OFFICE
CERTIFICATE OF CORRECTION

| | | |
|---|---|---|
| PATENT NO. | : 8,731,669 B2 | Page 1 of 1 |
| APPLICATION NO. | : 11/764886 | |
| DATED | : May 20, 2014 | |
| INVENTOR(S) | : Jordon D. Honeck, Andrew J. Ries and Karel F. A. A. Smits | |

It is certified that error appears in the above-identified patent and that said Letters Patent is hereby corrected as shown below:

IN THE CLAIMS:

Claim 6, Column 10, line 8, delete "... between the in receptacle and the ..." and insert in place thereof -- "... between the pin receptacle and the ..." --

Signed and Sealed this

Thirteenth Day of January, 2015

Michelle K. Lee
*Deputy Director of the United States Patent and Trademark Office*